(12) United States Patent
Joglekar et al.

(10) Patent No.: US 9,566,450 B2
(45) Date of Patent: Feb. 14, 2017

(54) MEDICAL DEVICE COMMUNICATION WITH WIRELESS TELEMETRY HEAD

(71) Applicant: Medtronic, Inc., Minneapolis, MN (US)

(72) Inventors: Ajinkya M. Joglekar, Maple Grove, MN (US); Warren W. Ball, Coon Rapids, MN (US); Timmothy S. Carlson, Fridley, MN (US); Matthew L. Plante, Stacy, MN (US)

(73) Assignee: Medtronic, Inc., Minneapolis, MN (US)

( * ) Notice: Subject to any disclaimer, the term of this patent is extended or adjusted under 35 U.S.C. 154(b) by 126 days.

(21) Appl. No.: 14/063,687

(22) Filed: Oct. 25, 2013

(65) Prior Publication Data

US 2015/0119846 A1   Apr. 30, 2015

(51) Int. Cl.
*A61N 1/372* (2006.01)
*A61N 1/378* (2006.01)
*A61M 5/142* (2006.01)

(52) U.S. Cl.
CPC ...... *A61N 1/37276* (2013.01); *A61M 5/14276* (2013.01); *A61N 1/378* (2013.01); *A61M 2205/3523* (2013.01); *A61M 2205/8206* (2013.01); *A61M 2209/01* (2013.01)

(58) Field of Classification Search
CPC ...... A61N 1/37276; A61N 1/378; A61N 1/36; A61B 5/002; A61B 5/0031; G06F 19/3468; A61M 2205/3592; A61M 5/142; A61M 2205/3507; A61M 2205/3523; A61M 2205/3569; A61M 5/16877

USPC ............... 604/891.1, 131, 151, 500
See application file for complete search history.

(56) References Cited

U.S. PATENT DOCUMENTS

| | | | |
|---|---|---|---|
| 6,456,883 B1* | 9/2002 | Torgerson et al. | 607/34 |
| 2003/0069614 A1* | 4/2003 | Bowman et al. | 607/60 |
| 2009/0125084 A1* | 5/2009 | Juels et al. | 607/60 |
| 2010/0130252 A1* | 5/2010 | Chishima | H04W 88/06 455/557 |
| 2011/0190853 A1* | 8/2011 | Dinsmoor | A61N 1/378 607/61 |
| 2011/0320130 A1* | 12/2011 | Valdes et al. | 702/19 |

* cited by examiner

*Primary Examiner* — Imani Hayman
*Assistant Examiner* — Hamza Darb
(74) *Attorney, Agent, or Firm* — Shumaker & Sieffert, P.A.

(57) ABSTRACT

In some examples, a method including wirelessly communicating, using an external medical device, with an implantable medical device via a telemetry head device, wherein the telemetry head device includes a power source configured to supply operational power to the telemetry head device; determining a first power level of the power source while the external medical device wirelessly communicates with the implantable medical device via the telemetry head device; suspending wireless communication between the implantable medical device and the external medical device based on the determined first power level. The wireless communication may be resumed, e.g., at the point communication was suspended, upon determining that the power level of the power source has been increased after the communication was suspended.

30 Claims, 7 Drawing Sheets

MEDICAL DEVICE COMMUNICATION WITH WIRELESS TELEMETRY HEAD

TECHNICAL FIELD

This disclosure relates generally to medical devices and, more particularly, to wireless communication between medical devices.

BACKGROUND

A variety of medical devices are used for chronic, i.e., long-term, delivery of fluid therapy to patients suffering from a variety of conditions, such as chronic pain, tremor, Parkinson's disease, epilepsy, urinary or fecal incontinence, sexual dysfunction, obesity, spasticity, or gastroparesis. For example, pumps or other fluid delivery devices can be used for chronic delivery of therapeutic agents, such as drugs, to patients. These devices are intended to provide a patient with a therapeutic output to alleviate or assist with a variety of conditions. Typically, such devices are implanted in a patient and provide a therapeutic output under specified conditions on a recurring basis. As another example, One type of implantable fluid delivery device is a drug infusion device that can deliver a fluid medication to a patient at a selected site. A drug infusion device may be implanted at a location in the body of a patient and deliver a fluid medication through a catheter to a selected delivery site in the body. Drug infusion devices, such as implantable drug pumps, commonly include a reservoir for holding a supply of a therapeutic fluid, such as a drug, for delivery to a site in the patient. The fluid reservoir can be self-sealing and accessible through one or more ports. A pump is fluidly coupled to the reservoir for delivering the therapeutic substance to the patient. A catheter provides a pathway for delivering the therapeutic substance from the pump to the delivery site in the patient.

As another example, a variety of medical devices are used for chronic, e.g., long-term, delivery of electrical stimulation therapy to patients suffering from conditions that range from chronic pain, tremor, Parkinson's disease, and epilepsy, to urinary or fecal incontinence, sexual dysfunction, obesity, spasticity, and gastroparesis. As an example, electrical stimulation generators are used for chronic delivery of electrical stimulation therapies such as neurostimulation, muscle stimulation, target organ stimulation, or the like. Electrical stimulation may be delivered in the form of series of electrical pulses that form a stimulation waveform that may be characterized by a number of the different shapes and forms. Typically, such devices provide therapy continuously or periodically according to parameters contained within a program. A program may comprise respective values for each parameter in a set of therapeutic parameters specified by a clinician. For example, a program may define characteristics of the electrical pulses defining the stimulation waveform, including pulse width, pulse frequency, constant voltage or constant current amplitude, and electrode polarity (anode or cathode).

SUMMARY

In some aspects, the disclosure relates to techniques for programming or otherwise communicating, via an external device, such as e.g., an external programmer, with a medical device, such as, e.g., an implantable medical device (IMD), that delivers medical therapy to a patient. The external device may wirelessly communicate with the medical device by way of an external telemetry head device that functions as an intermediary between the external device and medical device. For example, the external telemetry head device may include one or more telemetry modules configured to wirelessly communicate with a wireless telemetry module of the external device as well as one or more telemetry modules configured to wirelessly communicate with the medical device. Rather than the medical device and external device wirelessly communicating directly with each other, wireless communication between the devices may take place indirectly via the external telemetry head device. For example, an external device may transmit data to the wireless telemetry head device, which may then relay the data to the medical device, and vice versa.

In some examples, using such a wireless medical device system, during a programming session or other period when data is wirelessly transferred between an external programmer and medical device, the communication may be temporarily suspended if it is determined that the power level of the power source of the wireless telemetry head device is below some threshold level. While the communication session is suspended, the power source of the wireless telemetry head device may be recharged or replaced, or the entire wireless telemetry head device may be replaced with a different device with another power source. In this manner, the level of the power source may be increased to a level suitable for continuing wireless transmittal of data between the medical device and external programmer via the wireless telemetry head device. Once the power level of the power source reaches such a suitable level, the wireless communication may resume, e.g., at substantially the same point that the communication was suspended, rather than retransmitting all the data that had been transmitted between the programmer and medical device prior to the communication being suspended.

In one example, the disclosure relates to a method comprising wirelessly communicating, using an external medical device, with an implantable medical device via a telemetry head device, wherein the telemetry head device includes a power source configured to supply operational power to the telemetry head device; determining a first power level of the power source while the external medical device wirelessly communicates with the implantable medical device via the telemetry head device; suspending wireless communication between the implantable medical device and the external medical device based on the determined first power level, subsequently determining the power source increased to a second power level greater than the first power level; and resuming the suspended wireless communication between the implantable medical device and the external medical device via the telemetry head device based on the determined second power level of the power source, and wherein at least one of the communicating, determining, and suspending is performed via at least one processor.

In another example, the disclosure relates to a system comprising an external medical device; a telemetry head device, wherein the external medical device is configured to wirelessly communicate with an implantable medical device via the telemetry head device, wherein the telemetry head device includes a power source configured to supply operational power to the telemetry head device; and at least one processor configured to determine a first power level of the power source while the external medical device wirelessly communicates with the implantable medical device via the telemetry head device, suspend wireless communication between the medical device and the external medical device based on the determined first power level, subsequently determine the power source increased to a second power level greater than the first power level, and resume the suspended wireless communication between the implantable medical device and the external medical device via the telemetry head device based on the determined second power level of the power source.

In another example, the disclosure relates to a system comprising means for wirelessly communicating, using an external medical device, with an implantable medical device via a telemetry head device, wherein the telemetry head device includes a power source configured to supply operational power to the telemetry head device; means for determining a first power level of the power source while the external medical device wirelessly communicates with the implantable medical device via the telemetry head device; means for suspending wireless communication between the implantable medical device and the external medical device based on the determined first power level; means for subsequently determining the power source increased to a second power level greater than the first power level; and means for resuming the suspended wireless communication between the implantable medical device and the external medical device via the telemetry head device based on the determined second power level of the power source.

In another example, the disclosure relates to a computer-readable storage medium comprising instructions that cause a processor to wirelessly communicate, using an external medical device, with an implantable medical device via a telemetry head device, wherein the telemetry head device includes a power source configured to supply operational power to the telemetry head device; determine a first power level of the power source while the external medical device wirelessly communicates with the implantable medical device via the telemetry head device; suspend wireless communication between the medical device and the external medical device based on the determined first power level; subsequently determine the power source increased to a second power level greater than the first power level; and resume the suspended wireless communication between the implantable medical device and the external medical device via the telemetry head device based on the determined second power level of the power source.

The details of one or more examples disclosed herein are set forth in the accompanying drawings and the description below. Other features, objects, and advantages will be apparent from the description and drawings, and from the claims.

DETAILED DESCRIPTION

Figure 1:
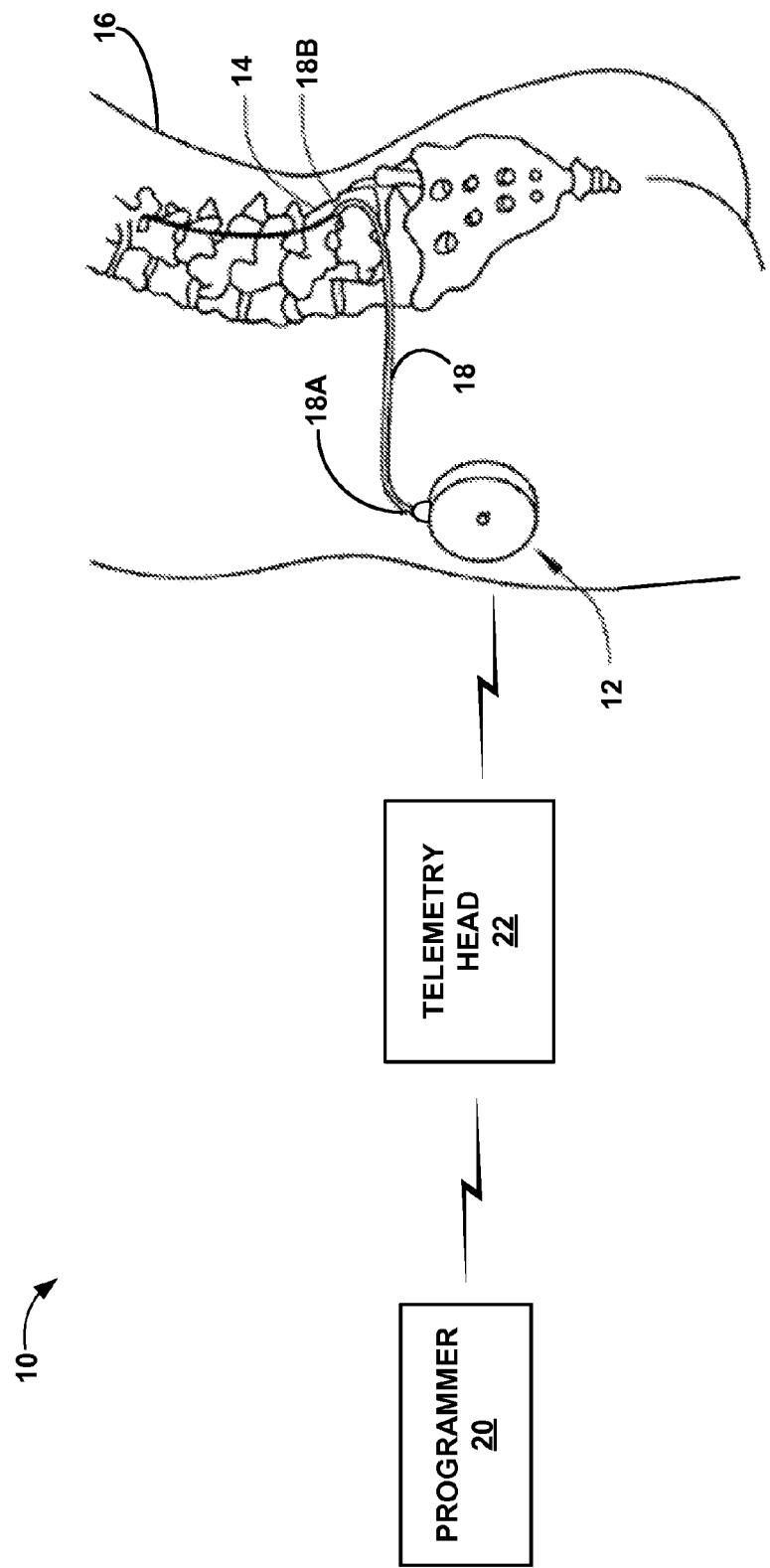
FIG. 1 is a conceptual diagram illustrating an example of a medical fluid delivery system.

In some aspects, the disclosure relates to techniques for programming, interrogating, or otherwise communicating via an external programmer with a medical device, such as, e.g., an implantable medical device (IMD), that delivers medical therapy to a patient. For example, the medical device may be configured to deliver therapy to a patient in the form of electrical stimulation therapy and/or monitor one or more physiological parameters of a patient. In some examples, the medical device may take the form of a medical fluid delivery device configured to deliver one or more therapeutic fluids to a patient to treat a patient condition and/or monitor one or more physiological parameters of a patient.

A clinician or other user may use an external medical device to communicate with a medical device. For example, a clinician may use an external medical device programmer to program one or more aspects of the therapy delivered to the patient. The external programmer may communicate with the medical device via wireless telemetry, particularly in cases in which the medical device is an IMD implanted within the patient. In some examples, the antenna and electronics used for the wireless communication may be contained within the housing of the external programmer. Alternatively, the antenna and related electronics may be contained with a telemetry head device that is tethered to the programmer via one or more short electrical wires that provide a wired connection between the programmer and telemetry head device. In such a configuration, a user may more easily align the antenna of the telemetry head device with the corresponding antenna of an IMD during interrogation, e.g., during a programming session, while still being able to view the user interface and otherwise interact with the external programmer. Further, the wired connection between the external programmer and telemetry head device may allow for operational power to be provided entirely by the power source (e.g., battery) of the external programmer.

However, in cases in which programming or other communication with an IMD by an external medical device takes place during the implantation of the IMD in the patient, both the external medical device and telemetry head may need to be sterilized for use within the operating room. Further, in some examples, due to the relatively close proximity between the telemetry head antenna and IMD antenna required for wireless communication, a clinician may be required to be within the operating room during such programming, e.g., rather than a separate room, or a relatively long wire must connect the telemetry head device to the programmer, which may be undesirable.

In accordance with some examples of the disclosure, a medical device system may include an external medical device such as an external programmer, an external telemetry head device (also referred to as "external telemetry head" or "telemetry head"), and a medical device, such as an IMD. Rather than a wired connection, the external medical device may be configured for wireless communication with an external telemetry head. Additionally, the external medical device may wirelessly communicate with the IMD by way of the external telemetry head device that functions as an intermediary between the programmer and medical device. For example, the external telemetry head may include one or more telemetry modules configured to wirelessly communicate with a wireless telemetry module of the external medical device as well as one or more telemetry modules configured to wirelessly communicate with the medical device. Rather than the IMD and external medical device wirelessly communicating directly with each other using a telemetry head wired to the external medical device, wireless communication between the IMD and external medical device may take place indirectly via the external telemetry head device. For example, an external medical device may transmit data to the wireless telemetry head device, which may then relay the data to the IMD, and vice versa.

For ease of illustration, examples of the disclosure are described for cases in which the external medical device takes the form of an external medical device programmer. However, examples of the external medical device are not limited as such. For example, in some cases, the medical device system need not include an external programmer, but may instead include some other type of external medical device, such as a smart phone, a dedicated monitoring device, or some other external device configured to communicate wirelessly with the external telemetry head. Such an external device may be configured for two-way communication with the external telemetry head to both send data to, and receive data from, the IMD. Alternatively, the external device may be limited to one-way communication with the IMD via the telemetry head such that, for example, the external device only receives data from, or only provides data to, the IMD. In one example, the external device may be limited to receiving data, such as physiological data sensed from the patient, from the IMD via the external telemetry head. Thus, while the following disclosure primarily discusses use of an external programmer, it will be understood that this is by way of example, and other types of external devices may usefully employ techniques described herein.

The wireless communication relationship of the external telemetry head device and the programmer may not allow for operational power for the telemetry head device to be supplied by the programmer. Instead, the external telemetry head device may include a power source, e.g., rechargeable lithium ion or alkaline, batteries within its housing, used for operational power, separate from that of the power source of the external programmer. The power source of the external telemetry device may supply power in an amount that allows the external telemetry head device to wirelessly communicate with an IMD and external programmer as described herein.

In some examples, the power level of such a power source may be determined before or during a period of wireless communication between an IMD and programmer via the external telemetry head device. The wireless communication between the two devices via the external telemetry head device includes the transfer of data between the IMD and programmer devices, and may take the form of one-way communication (i.e., only transfer of data from the IMD to programmer and vice versa) and/or two-way communication (i.e., transfer of data to and from the IMD and programmer). The data transferred between the IMD and programmer may include data transfer from the programmer to the IMD to define one of more aspects of the therapy delivered by the IMD to a patient (e.g., in the form of a therapy program) or the transfer of data stored on the memory of the IMD (e.g., data detailing one or more operational parameters of the IMD and/or one or more physiological parameters of a patient being monitored by the IMD) to the external device for evaluation by a clinician.

As one example, a programmer may wirelessly interrogate an IMD using the wireless communication link established via an external telemetry head. During an interrogation session, a series of commands (both single and multiple) may be sent to the IMD from the programmer to read the current configuration of the IMD, and additional data may be requested during the interrogation session. In such a scenario, the interrogation session may be viewed as the periodic transmission of smaller packets of data rather than the continuous flow of data from the programmer to IMD, and vice versa, via the external telemetry device. The interrogation session may end when all the requested data is received by the programmer from the IMD. In some examples, the interrogation session may be paused or suspended by stopping the transmission of the series of commands.

As another example, a programmer may wirelessly program an IMD using the wireless communication link established via external telemetry head. During the programming session, a clinician may define one or more aspects or values of therapy parameters (e.g., by defining one or more therapy programs) and write the data to the memory of the IMD using the wireless communication link established via the external telemetry head device. In some examples, a clinician may modify some of the data received during interrogation of the IMD using the programmer and then write the data back to the IMD memory using the wireless communication link.

In the case of a system which employs an external telemetry head device, as described in the disclosure, wireless communication may be initiated when data is first wirelessly transmitted from the external programmer to the IMD via the external telemetry device, or vice versa. In some examples, over the period of time during which the IMD and programmer wirelessly communicate via an external telemetry head device (which may also may be referred to as an "wireless communication session"), the power level of the telemetry head device's power source may be monitored, e.g., by one or more processors of the telemetry head device and/or programmer. If the power level is determined to be below a threshold level, the wireless communication session may be temporarily suspended, e.g., to recharge or replace the power source of the external telemetry device or even replace the telemetry head device with another telemetry head device. This suspension temporarily halts the transfer of data before all of the data intended for transfer during that communication session has, in fact, been transferred. This suspension may occur during the transmission of any type of data to, or from, the IMD, including programmed instructions, therapy or other operational parameters, physiological data sensed by the IMD, or any other type of data transferred between the external device and the IMD. In some examples, the data transferred prior to the suspension of the communication may be saved, e.g., in the memory of the IMD, but the changes related to the data, e.g., in term of therapy parameter value adjustments, may not implemented until the therapy is resumed and all the intended data is transferred to the IMD from the external programmer. When the suspended communication is resumed, the data transfer may be resumed at substantially the same point the communication was suspended, e.g., rather than resuming the communication by starting the data transfer from the beginning.

In some examples, the threshold power level may generally correspond to an amount of power that would not allow the telemetry head device to operate throughout, i.e., for the duration of, the entire communication session. Once the power level has been increased to a level sufficient to allow the telemetry device to operate throughout the remainder of the communication session, the wireless communication session may be resumed, e.g., at the point the communication (e.g., interrogation and/programming) was suspended, rather than requiring all of the data previously communicated prior to the suspension to be re-sent between the IMD and programmer via the external telemetry head device.

In some examples, during the wireless communication session, the communication between the programmer and IMD may include a command from the programmer and response to the command by the IMD. If the power level of the telemetry device battery source is determined to be too low, the programmer may suspend the transmission of commands until the power level has been increased to a level sufficient to allow the telemetry device to operate throughout the remainder of the communication session. As noted, the wireless communication session may be resumed at the point the communication (e.g., interrogation and/programming) was suspended rather than starting from the beginning. For example, each command and response may share a sequence number so the programmer will know that it gets the proper response from the IMD. With this information the programmer can start up where it was suspended, because it knows which command/response was last successfully completed. In some examples, the programmer, IMD, and telemetry head device may exchange security information (e.g., using a suitable wireless handshake technique) in order to resume the session.

In other examples, prior to initiating a programming/interrogation session or other session during which the external programmer wirelessly communicates an IMD, the medical device system may be configured to determine the power level of the external telemetry head device power source. If the power level of the power source is below some threshold level, the programmer may not initiate wireless communication between an IMD via the external telemetry head device. For example, the threshold power level may generally correspond to a power level at which the power source would not be capable of supplying operational power to the telemetry head device throughout the entire programming or interrogation session. Rather, the programmer may prompt the user to recharge or replace the batteries of the external telemetry head device, or utilize another telemetry head device with a different power source exhibiting a power level greater than the threshold level. Once the power level of the power source is determined to be at a level that is suitable for providing operational power to the telemetry head device throughout the entire programming or interrogation session, the session may be initiated and data may be transmitted wirelessly between the medical device and programmer via the telemetry head device.

In some examples, a user may initiate a programming, interrogation, or other wireless communication session using a user interface on the programming device. For example, a user may depress a button or navigate a touch screen to select an indicator that wireless communicates with the IMD using a wireless telemetry connection to indicate the communication session should begin. Upon receiving the user input, the programmer may attempt to initiate wireless communication with the IMD using wireless telemetry. In some examples, when attempting to initiate the interrogation of an IMD, a programmer must establish communication with the IMD within a certain period of time. If communication is not established during the time period, e.g., due to the telemetry head device being improperly positioned relative to the IMD, a clinician may be required to re-enter the initiation command for the programmer to re-attempt to initiate interrogation of the IMD.

For systems including a programmer with a wired connection to a telemetry head (e.g., a telemetry wand), a clinician may be required to use both hands (one to hold the programmer and one to hold the telemetry head) while communicating with an IMD. In some examples, such a configuration may result in a clinician attempting to initiate wireless communication of the IMD with the programmer before communication is actually ready to begin, e.g., when the telemetry head is not in proximity and/or alignment with the IMD. As a result, initiation of the interrogation might "time out," requiring the user to attempt to re-initiate the interrogation, possibly leading to a time consuming process and frustration by the clinician and patient.

Additionally, for systems in which a wireless telemetry head device is configured to wirelessly communicate with both the IMD and programmer, a user may not be in reach of the programmer when positioning the external telemetry head device to interact with the user interface of the programmer to initiate the interrogation of the IMD. As one example, in an operating room setting during implant of an IMD, a clinician may position a sterilized external telemetry head device for communication with an IMD within the sterile field (e.g., the external telemetry device may be contained within a sterile barrier and introduced into the sterile field) but the external programmer may be located outside the sterile field. In such cases, the user interface of the programmer may not be readily available to the clinician to indicate that wireless communication with the IMD should be initiated using the user interface of the programmer via the external telemetry head device without violating the sterile field.

In accordance with some examples of the disclosure, an external telemetry head device that is configured to wirelessly communicate with both an IMD and external programmer to facilitate communication between the IMD and programmer may also be configured to receive input from a user to initiate wireless communication between the programmer and IMD. For example, the external telemetry head device may include one or more buttons and/or other types of user interface employed to receive an indication from a user that a wireless communication session with the IMD should be initiated by the programmer. In response, the external telemetry head device may wirelessly communicate to the programmer that wireless communication with the IMD should be initiated, e.g., by starting a search and identification protocol to establish secure communication with the IMD via the wireless telemetry head device. In some examples, authorization to "remotely" initiate wireless communication in such a manner via a telemetry head device may be selectively enabled and disabled (e.g., via the external programmer) to prevent the inadvertent establishment of communication between the programmer and an IMD.

FIG. 1 is a conceptual diagram illustrating an example of a medical therapy system 10 for delivering a therapeutic fluid to patient 16. Therapy system 10 includes implantable medical device (IMD) 12, catheter 18, external programmer 20, and external telemetry head device 22. IMD 12 and external programmer 20 wirelessly communicate with via telemetry head device 22. External programmer 20 may wirelessly communicate with IMD 12 by way of external telemetry head device 22 that functions as an intermediary between programmer 20 and IMD 12. For example, as will be described further below, external telemetry head device 22 may include one or more telemetry modules configured to wirelessly communicate with a wireless telemetry module of external programmer 20 as well as one or more telemetry modules configured to wirelessly communicate with a telemetry module of IMD 12. In this manner, rather than IMD 12 and external programmer 20 wirelessly communicating directly with each other, wireless communication between the devices may take place indirectly via the external telemetry head device 22. For example, external programmer 20 may transmit data to wireless telemetry head device 22, which may then relay the data to IMD 12, and vice versa.

Examples of the disclosure are primarily described with regard to medical fluid delivery systems and devices for purposes of illustration. However, the disclosure is not limited to such examples. In some examples, the techniques described in this disclosure may be generally applicable to a variety of medical device systems including external and implantable medical devices (IMDs). In some examples, one or more of the techniques described in this disclosure may be applied to therapy systems including external or internal electrical stimulators such as, e.g., neurostimulators that deliver neuro stimulation therapy to a patient or cardiac stimulator devices that deliver pacing, cardioversion and/or defibrillation stimulation to the heart of a patient. In one example, the techniques described herein may be applicable to implantable spinal cord stimulator (SCS) system that delivers electrical SCS, e.g., for relief of chronic pain or other symptoms. In some examples, the electrical stimulation therapy delivered to a patient by the medical device system may be used to treat tremor, Parkinson's disease, epilepsy, urinary or fecal incontinence, pelvic pain, sexual dysfunction, obesity, gastroparesis, or psychiatric disorders (e.g., depression, mania, obsessive compulsive disorder, anxiety disorders, and the like). In this manner, such a medical device system may be configured to provide therapy taking the form of deep brain stimulation (DBS), pelvic floor stimulation, gastric stimulation, or any other electrical stimulation therapy.

Therapy system 10 delivers a medical therapy to patient 16. In the example of FIG. 1, IMD 12 is connected to catheter 18 to deliver at least one therapeutic fluid agent, such as a pharmaceutical agent, pain relieving agent, anti-inflammatory agent, gene therapy agent, or the like, to a target site within patient 16. IMD 12 may include a reservoir, pump and controller for delivery of a therapeutic fluid via catheter 18. IMD 12 and catheter 18 together form an implantable fluid delivery device. Additionally or alternatively, IMD 12 may be configured to deliver a therapeutic fluid to patient 16 without catheter 18, e.g., via one or more delivery ports formed in the housing of IMD 12. In the example of FIG. 1, the fluid delivery device is fully implantable within the patient, but may communicate with external devices such as programmer 20 or network 22 via wireless telemetry, and receive refill of therapeutic fluid via percutaneous injection. In other examples, the fluid delivery device may be partially implantable. For example, the reservoir, pump and controller may be external to the patient, while catheter 18 may be implantable within the patient, and coupled to the external pump via a percutaneous port. Hence, the techniques described in this disclosure may be especially useful with fully implantable fluid delivery device including implantable reservoir, pump, controller and catheter, but also may be used with a partially implantable fluid delivery device or external fluid delivery device.

In the example of FIG. 1, the therapeutic agent is a therapeutic fluid, which IMD 12 delivers to patient 16 through catheter 18 from a proximal end 18A coupled to IMD 12 to distal end 18B located proximate to the target site. Catheter 18 can comprise a unitary catheter or a plurality of catheter segments connected together to form an overall catheter length. External programmer 20 is configured to wirelessly communicate with IMD 12 as needed, such as to provide or retrieve therapy information or control aspects of therapy delivery (e.g., modify the therapy parameters such as rate or timing of delivery, turn IMD 12 on or off, and so forth) from IMD 12 to patient 16.

IMD 12 may have an outer housing that is constructed of a biocompatible material that resists corrosion and degradation from bodily fluids including, e.g., titanium or biologically inert polymers. IMD 12 may be implanted within a subcutaneous pocket relatively close to the therapy delivery site. For example, in the example shown in FIG. 1, IMD 12 is implanted within an abdomen of patient 16. In other examples, IMD 12 may be implanted within other suitable sites within patient 16, which may depend, for example, on the target site within patient 16 for the delivery of the therapeutic agent. In still other examples, as discussed above, instead of providing fully implantable IMD 12, one or more components of IMD 12 may be external to patient 16 with a percutaneous catheter connected between such components and the target delivery site within patient 16, providing an at least partially implantable fluid delivery device. In general, however, fully implantable fluid delivery devices are described in this disclosure for purposes of illustration.

In the example shown in FIG. 1, catheter 18 traverses from the implant site of IMD 12 to one or more targets proximate to spine 14. Catheter 18 is positioned such that one or more fluid delivery outlets (not shown in FIG. 1) of catheter 18 are proximate to the targets within patient 16. In the example of FIG. 1, IMD 12 delivers a therapeutic agent through catheter 18 to targets proximate to spinal cord 14. Although the target site shown in FIG. 1 is proximate to spinal cord 14 of patient 16, other applications of therapy system 10 include alternative target delivery sites. The target delivery site in other applications of therapy system 10 can be located within patient 16 proximate to, e.g., sacral nerves (e.g., the S2, S3, or S4 sacral nerves), brain, or any other suitable nerve, organ, muscle or muscle group in patient 16, which may be selected based on, for example, a patient condition.

In some examples, IMD 12 may include a sensor used to monitor information related to the delivery of therapy to patient 16. In some examples, a sensor may be configured to collect information regarding the efficacy of therapy being delivered by IMD 12 and/or side effects resulting from the therapy. Information collected by the sensor may be used by therapy system 10 to identify the need to initiate, terminate, and/or adjust the delivery of therapy to patient 16 from IMD 12. Data collected by the sensor may be communicated to programmer 20 from IMD 12 via telemetry head 22.

Programmer 20 is an external computing device that is configured to communicate with IMD 12 via wireless telemetry. In some examples, programmer 20 may be a hand-held computing device that includes a display viewable by the user and a user input mechanism that can be used to provide input to programmer 20. For example, programmer 20 may include a display screen (e.g., a liquid crystal display or a light emitting diode display) that presents information to the user. In addition, programmer 20 may include a keypad, buttons, a peripheral pointing device, touch screen, voice recognition, or another input mechanism that allows the user to navigate though the user interface of programmer 20 and provide input. In some examples, a clinician may utilize a programmer 20 to interrogate IMD 12 to make changes to the therapy parameter settings. The clinician programmer may include additional or alternative programming features relative to the patient programmer. For example, more complex or sensitive tasks may only be allowed by the clinician programmer to prevent patient 16 from making undesired or unsafe changes to the operation of IMD 12.

If programmer 20 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 20 may be a touch screen that allows the user to provide input directly to the user interface shown on the display. The user may use a stylus or his/her finger to provide input to the display.

In other examples, rather than being a handheld computing device or a dedicated computing device, programmer 20 may be a larger workstation or a separate application within another multi-function device. For example, the multi-function device may be a cellular phone, personal computer, laptop, workstation computer, or personal digital assistant that can be configured with an application to simulate programmer 20. Alternatively, a notebook computer, tablet computer, or other personal computer may enter an application to become programmer 20 with a wireless adapter connected to the personal computer for communicating with IMD 12.

As noted above, in some cases, programmer 20 may be an external device such as a cellular phone or some other monitoring device that need not be configured to transfer data to IMD 12, but may instead be limited to receiving data from IMD 12 (e.g., for monitoring purposes.) In yet other examples, the programmer 20 may be an external device configured solely to transfer data to the IMD 12, but not to receive data from the IMD.

When programmer 20 is configured for use by the clinician, programmer 20 may be used to transmit initial programming information to IMD 12. This initial information may include hardware information for system 10 such as the type of catheter 18, the position of catheter 18 within patient 16, the type and amount, e.g., by volume of therapeutic agent(s) delivered by IMD 12, a refill interval for the therapeutic agent(s), a baseline orientation of at least a portion of IMD 12 relative to a reference point, therapy parameters of therapy programs stored within IMD 12 or within programmer 20, and any other information the clinician desires to program into IMD 12.

The clinician uses programmer 20 to program IMD 12 with one or more therapy programs that define the therapy delivered by the IMD. During a programming session, the clinician may define one or more therapy programs that may provide effective therapy to patient 16. Patient 16 may provide feedback to the clinician as to efficacy of a program being evaluated or desired modifications to the program. Once the clinician has identified one or more programs that may be beneficial to patient 16, the patient may continue the evaluation process and determine which therapy program best alleviates the condition of the patient or otherwise provides efficacious therapy to the patient.

In some cases, programmer 20 may also be configured for use by patient 16. When configured as the patient programmer, programmer 20 may have limited functionality in order to prevent patient 16 from altering critical functions or applications that may be detrimental to patient 16. In this manner, programmer 20 may only allow patient 16 to adjust certain therapy parameters or set an available range for a particular therapy parameter. In some cases, a patient programmer may permit the patient to control IMD 12 to deliver a supplemental, patient bolus, if permitted by the applicable therapy program administered by the IMD, e.g., if delivery of a patient bolus would not violate a lockout interval or maximum dosage limit.

Whether programmer 20 is configured for clinician or patient use, programmer 20 may wirelessly communicate to IMD 12 by way of external telemetry head device 22. In particular, programmer 20 may wirelessly communicate with external telemetry head device 22. Telemetry head device 22 may then relay all or part of the communication from programmer 20 to IMD 12 via wireless telemetry. Similarly, IMD 12 may wirelessly communicate with external telemetry head device 22, and the telemetry head device 22 may then relay all or part of the communication from IMD 12 to programmer 20 via wireless telemetry.

Any suitable standard or proprietary wireless telemetry techniques may be utilized for direct wireless communication between programmer 20 and telemetry head 22 as well as between telemetry head 22 and IMD 12. The wireless telemetry technique for direct wireless communication between programmer 20 and telemetry head 22 may be the same or different from the wireless telemetry technique used for direct wireless telemetry between telemetry head 22 and IMD 12. In some examples, telemetry head 22 may communicate via wireless communication with IMD 12 and/or programmer 20 using inductive telemetry techniques, radio frequency (RF) telemetry techniques, Bluetooth specification sets, infrared (IR) communication according to the IRDA specification set (for communication with programmer 20), or other standard or proprietary telemetry protocols. These telemetry techniques may relate to short-range "proximal" communication schemes that communicate over a relatively short distance (e.g., measured in centimeters), or may relate to longer distance techniques such as "arm's length communication" mechanisms or techniques involving communication over a distance of several meters or more.

Communication between IMD 12 and programmer 20 by way of telemetry head device 22 may allow one-way or two-way wireless transfer of information between IMD 12 and programmer 20. In some examples, data may be transferred during a programming session to allow a clinician or other user to define or redefine one of more therapy programs used by IMD 12 to control the delivery of therapy to patient 16. In other examples, programmer 20 may retrieve data stored on the memory of IMD 12 relating to one or more patient parameters monitored by IMD 12 or details of therapy previously delivered to patient 16. Other types of data communications between IMD 12 and programmer 20 via telemetry head 22 are contemplated.

Figure 2:
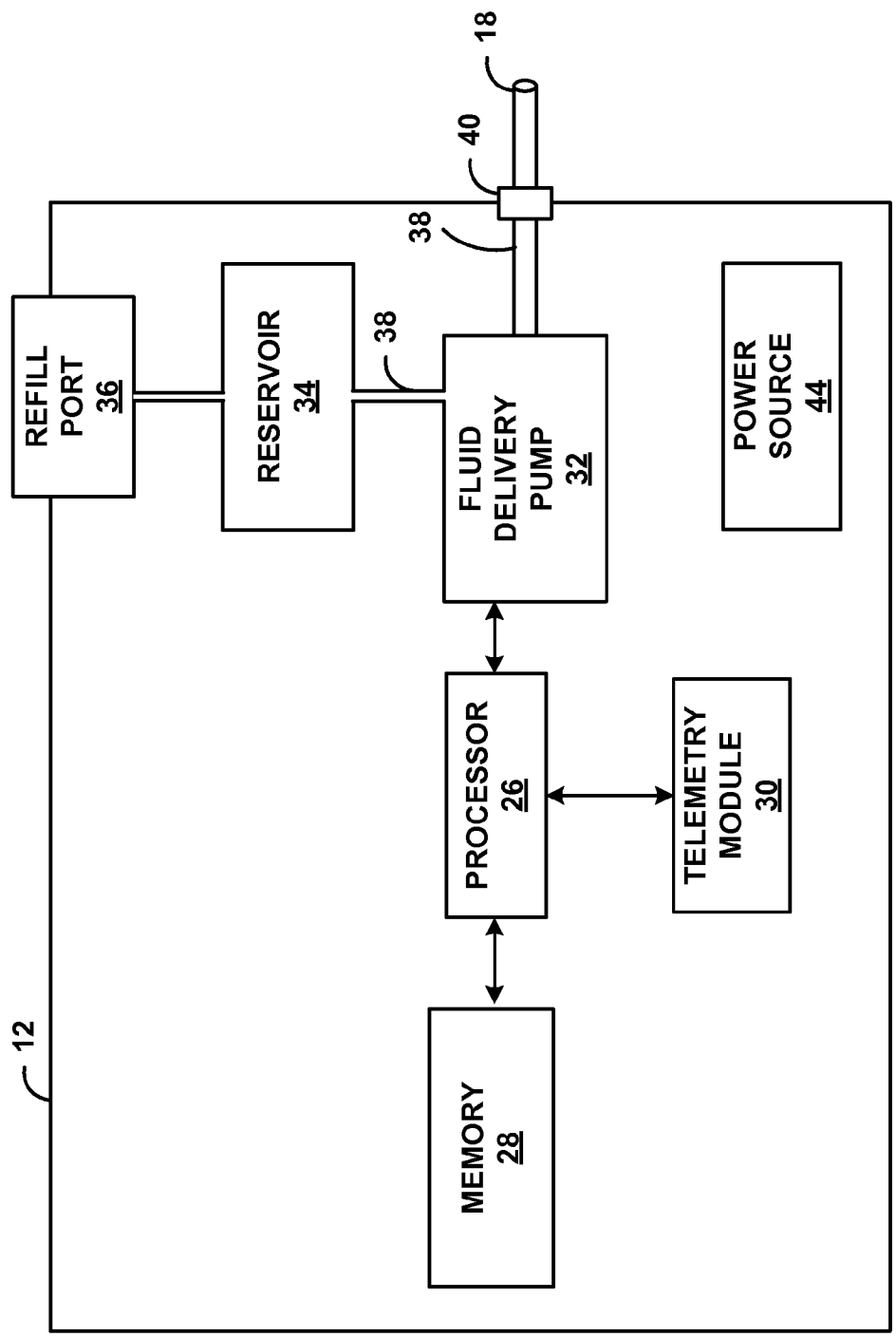
FIG. 2 is functional block diagram illustrating an example of the implantable fluid delivery device.

FIG. 2 is a functional block diagram illustrating components of an example of IMD 12, which includes processor 26, memory 28, telemetry module 30, fluid delivery pump 32, reservoir 34, refill port 36, internal tubing 38, catheter access port 40, and power source 44. Processor 26 is communicatively connected to memory 28, telemetry module 30, and fluid delivery pump 32. Fluid delivery pump 32 is connected to reservoir 34 and internal tubing 38. Reservoir 34 is connected to refill port 36. Catheter access port 40 is connected to internal tubing 38 and catheter 18. IMD 12 also includes power source 44, which is configured to deliver operating power to various components of IMD 12.

During operation of IMD 12, processor 26 operates as a controller that controls fluid delivery pump 32 with the aid of instructions associated with therapy program information 29 that is stored in memory 28 to deliver a therapeutic agent to patient 16 via catheter 18. Instructions executed by processor 26 may, for example, be defined by one or more therapy programs that specify the amount of a therapeutic agent that is delivered to a target tissue site within patient 16 from reservoir 30 via catheter 18. The instructions may further specify the time at which the agent will be delivered and the time interval over which the agent will be delivered. The therapy programs may also include other therapy parameters, such as the frequency of bolus delivery, the type of therapeutic agent delivered if IMD 12 is configured to deliver more than one type of therapeutic agent, and so forth. Components described as processors within IMD 12, external programmer 20, external telemetry device 22, or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Upon instruction from processor 26, fluid delivery pump 32 draws fluid from reservoir 34 and pumps the fluid through internal tubing 38 to catheter 18 through which the fluid is delivered to patient 16 to effect one or more of the treatments described above. Internal tubing 38 is a segment of tubing or a series of cavities within IMD 12 that run from reservoir 34, around or through fluid delivery pump 32 to catheter access port 40. Fluid delivery pump 32 can be any mechanism that delivers a therapeutic agent in some metered or other desired flow dosage to the therapy site within patient 16 from reservoir 30 via implanted catheter 18. Periodically, fluid may need to be supplied percutaneously to reservoir 34 because all of a therapeutic agent has been or will be delivered to patient 16, or because a clinician wishes to replace an existing agent with a different agent or similar agent with different concentrations of therapeutic ingredients. Refill port 26 can therefore comprise a self-sealing membrane to prevent loss of therapeutic agent delivered to reservoir 30 via refill port 26.

Memory 28 of IMD 12 may store therapy program information 29 including instructions for execution by processor 26, such as, but not limited to, therapy programs, historical therapy programs, timing programs for delivery of fluid from reservoir 34 to catheter 18, and any other information regarding therapy of patient 16. Memory 28 may include separate memories for storing instructions, patient information, therapy parameters, therapy adjustment information, program histories, and other categories of information such as any other data that may benefit from separate physical memory modules. Therapy adjustment information may include information relating to timing, frequency, rates and amounts of patient boluses or other permitted patient modifications to therapy. In some examples, memory 28 stores program instructions that, when executed by processor 26, cause IMD 12 and processor 26 to perform the functions attributed to them in this disclosure.

At various times during the operation of IMD 12 to treat patient 16, communication to and/or from IMD 12 may be necessary to, e.g., change therapy programs, adjust parameters within one or more programs, or to otherwise download information to or from IMD 12. Processor 26 therefore controls telemetry module 30 to wirelessly communicate between IMD 12 and programmer 20 by wirelessly communicating with telemetry head 22. As noted above, any suitable type of wireless telemetry techniques may be utilized. Telemetry module 30 in IMD 12, as well as telemetry modules in other devices described in this disclosure, such as programmer 20 and telemetry head 22, can be configured to use RF communication techniques to wirelessly send and receive information to and from other devices respectively. To support RF communication, telemetry module 56 as well as the telemetry modules of programmer 20 and telemetry head 22 may include appropriate electronic components, such as amplifiers, filters, mixers, encoders, decoders, and the like. As another example, telemetry module 30 may communicate with programmer 20 via proximal inductive interaction between IMD 12 and telemetry head device 22. Telemetry module 30 may send information to external programmer 20 via telemetry head device 22 upon request from programmer 20.

Power source 44 delivers operating power to various components of IMD 12. Power source 44 may include a small rechargeable or non-rechargeable battery and a power generation circuit to produce the operating power. In the case of a rechargeable battery, recharging may be accomplished through proximal inductive interaction between an external charger and an inductive charging coil within IMD 12. In some examples, power requirements may be small enough to allow IMD 12 to utilize patient motion and implement a kinetic energy-scavenging device to trickle charge a rechargeable battery. In other examples, traditional batteries may be used for a limited period of time. As another alternative, an external inductive power supply could transcutaneously power IMD 12 as needed or desired.

Figure 3:
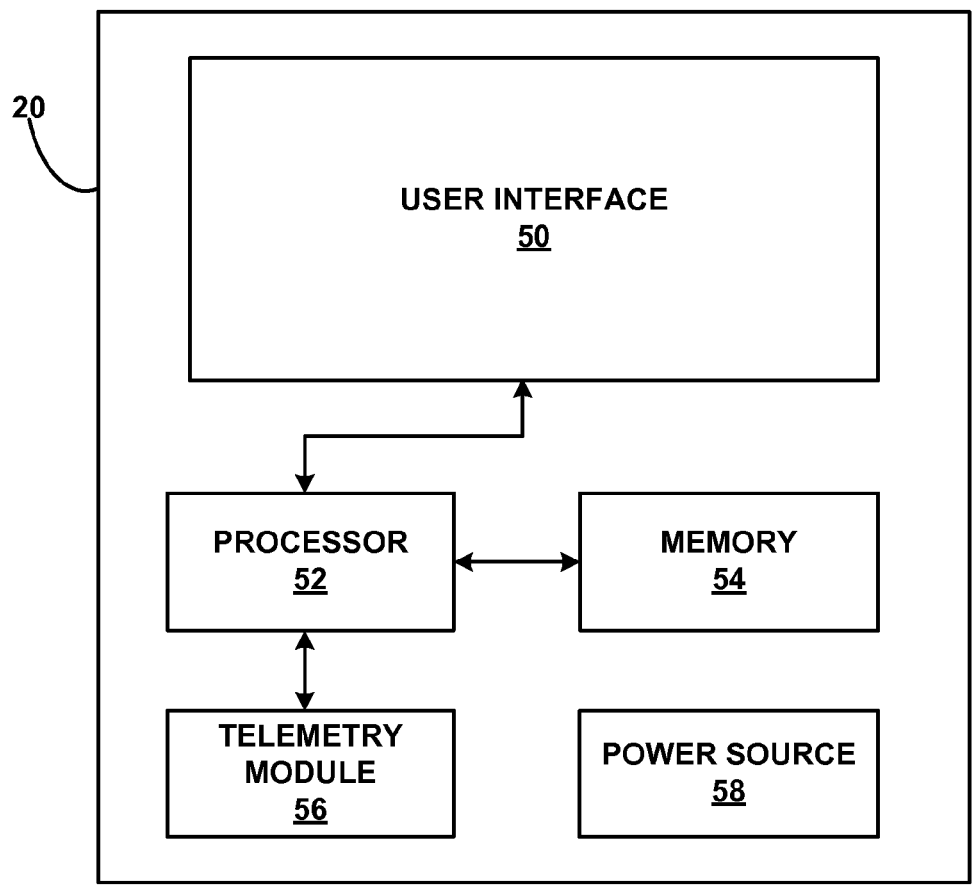
FIG. 3 is a functional block diagram illustrating an example of an external medical device.

FIG. 3 is a functional block diagram illustrating various components of external programmer 20 for IMD 12. As shown in FIG. 3, external programmer 20 includes user interface 50, processor 52, memory 54, telemetry module 56, and power source 58. A clinician or patient 16 interacts with user interface 50 in order to manually change the parameters of a therapy program, change therapy programs within a group of therapy programs, view therapy information, view historical therapy regimens, establish new therapy regimens, or otherwise communicate with IMD 12 or view or edit programming information.

User interface 50 may include a screen and one or more input buttons, as discussed in greater detail below, that allow external programmer 20 to receive input from a user. Alternatively or additionally, user interface 50 may additionally or only utilize a touch screen display. The screen may be a liquid crystal display (LCD), dot matrix display, organic light-emitting diode (OLED) display, touch screen, or any other device capable of delivering and/or accepting information. For visible indications of therapy program parameters or operational status, a display screen may suffice. For audible and/or tactile indications of therapy program parameters or operational status, programmer 20 may further include one or more audio speakers, voice synthesizer chips, piezoelectric buzzers, or the like.

Input buttons for user interface 50 may include a touch pad, increase and decrease buttons, emergency shut off button, and other buttons needed to control the therapy, as described above with regard to patient programmer 20. Processor 52 controls user interface 50, retrieves data from memory 54 and stores data within memory 54. Processor 52 also controls the wireless transmission of data through telemetry module 56 to IMD 12 by transmitting data to telemetry head 22, which then transmits data to IMD 12. The transmitted data may include therapy program information specifying various drug delivery program parameters. Memory 54 may include operational instructions for processor 52 and data related to therapy for patient 16. Memory 54 may additionally or alternatively store all or some of the information described above as being stored in memory 28 of IMD 28, and vice versa.

User interface 50 may be configured to present therapy program information to the user. User interface 50 enables a user to program IMD 12 in accordance with one or more dosing programs, therapy schedules, or the like. For example, a user such as a clinician, physician or other caregiver may input patient information, drug information including expiration time of the drug, therapy schedules, priming information, bridging information, drug/IMD implant location information, or other information to programmer 20 via user interface 50. In addition, user interface 50 may display therapy program information as graphical bar graphs or charts, numerical spread sheets, or in any other manner in which information may be displayed. Further, user interface 50 may present nominal or suggested therapy parameters that the user may accept via user interface 50.

Power source 58 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter. In some examples, external programmer 20 may be configured to recharge IMD 12 in addition to programming IMD 12.

Figure 4:
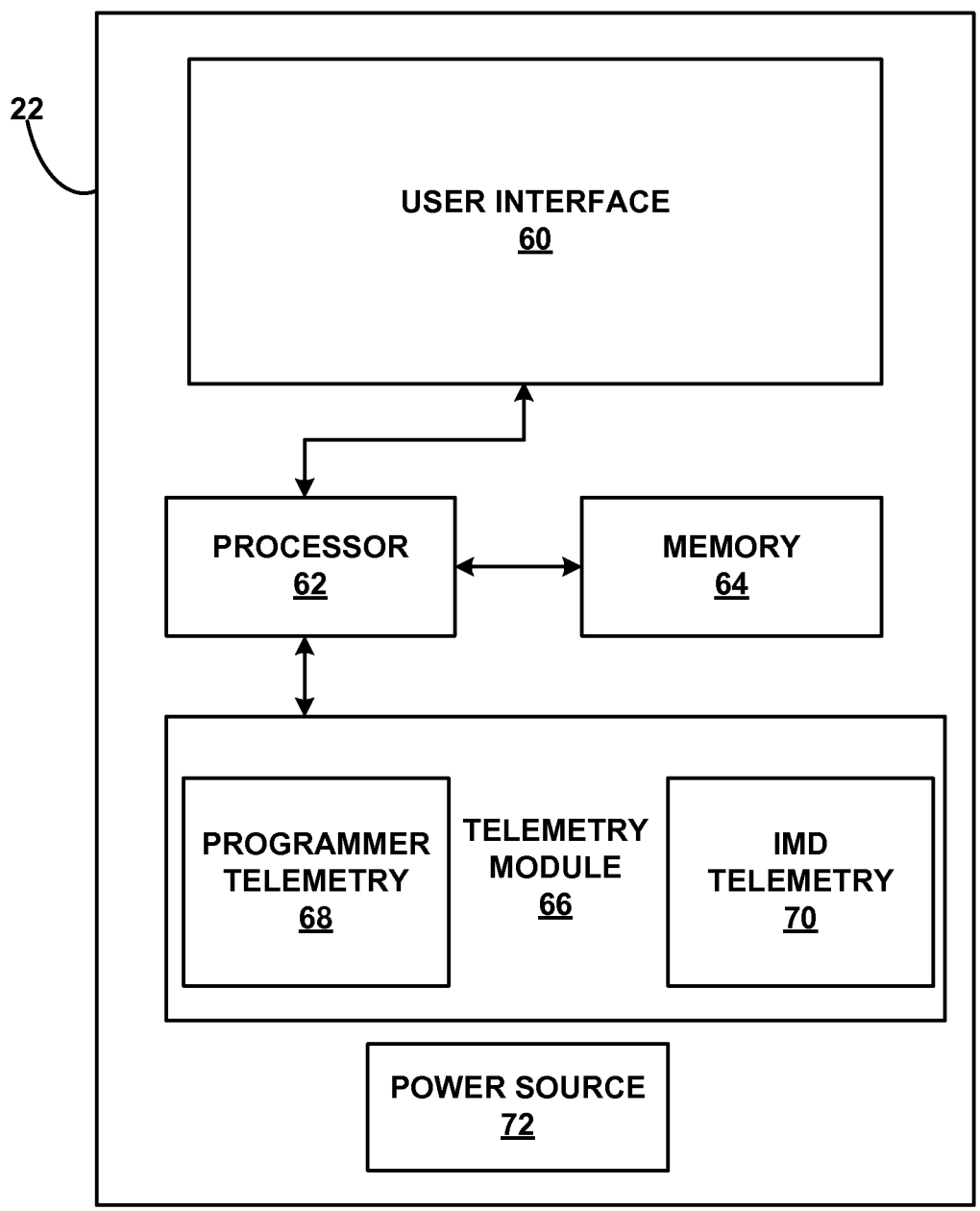
FIG. 4 is a functional block diagram illustrating an example of a telemetry device head.

FIG. 4 is a functional block diagram illustrating an example of a telemetry device head. Telemetry head device 22 includes user interface 60, processor 62, memory 64, telemetry module 66, and power source 72. As described herein, telemetry head device 22 may be configured to wirelessly communicate with both IMD 12 and programmer 20. With such functionality, programmer 20 and IMD 12 may wirelessly transfer data between each other using telemetry head device 22 as an intermediary.

Processor 62 may control telemetry module 66 to wirelessly communicate with both IMD 12 and programmer 20. As shown in FIG. 4, telemetry module 66 includes programmer telemetry module 68 and IMD telemetry module 70. Programmer telemetry module 68 may include circuitry and one or more antennas configured to wirelessly communicate with telemetry module 56 of programmer 20. Likewise, IMD telemetry module 70 may include circuitry and one or more antennas configured to wirelessly communicate with telemetry module 30 of IMD 12. Programmer telemetry module 68 and IMD telemetry module 70 may be configured to utilize any suitable wireless telemetry techniques to allow telemetry head device 22 to wirelessly transfer data between programmer 20 and IMD 12 in the manner described herein. Programmer telemetry module 68 and IMD telemetry module 70 may be configured to utilize the same or different wireless telemetry techniques for communication with programmer 20 and IMD 12, respectively.

Memory 64 stores program instructions that, when executed by processor 62, cause telemetry device 22 and processor 62 to perform the functions attributed to them in this disclosure. For example, memory 64 may store instructions that, when executed by processor 62, cause processor 62 to wirelessly communicate with IMD 12 using IMD telemetry module 70 and wirelessly communicate with programmer 20 using programmer telemetry module 68. Memory may also store information relating to the power level of power source 72, e.g., for use by processor 62 and/or processor 52 to determine the power level of power source 72 at one time during or before interrogation of IMD 12 by programmer 20 using telemetry device 22.

User interface 60 may be substantially the same or similar to that of user interface 50 of programmer 20, and may allow a user to interact with the function of telemetry head device 22. As described herein, in some examples, a user may interact with user interface 60 of telemetry head 22 to indicate to the telemetry head device 22 that interrogation of IMD 12 by programmer 20 should be initiated. In some examples, user interface 60 may present an indicator of the power level of power source 72 to a user.

Power source 72 is separate from that of power source 58 of programmer 58, and may provide operational power for telemetry head device 22 to function as described herein. Similar to power source 58 of programmer 20, power source 72 may be a rechargeable battery, such as a lithium ion or nickel metal hydride battery. Other rechargeable or conventional primary batteries may also be used. In some cases, external programmer 20 may be used when coupled to an alternating current (AC) outlet, i.e., AC line power. As described further below, the power level of power source 58 may decrease, e.g., through use of external head device 22 for wireless communication between IMD 12 and programmer 20. In some examples, communication between programmer 20 and IMD 12 via external head device 22 may be temporarily suspended or even prevented from being initiated based on the power level of telemetry head device power source 58.

Figure 5:
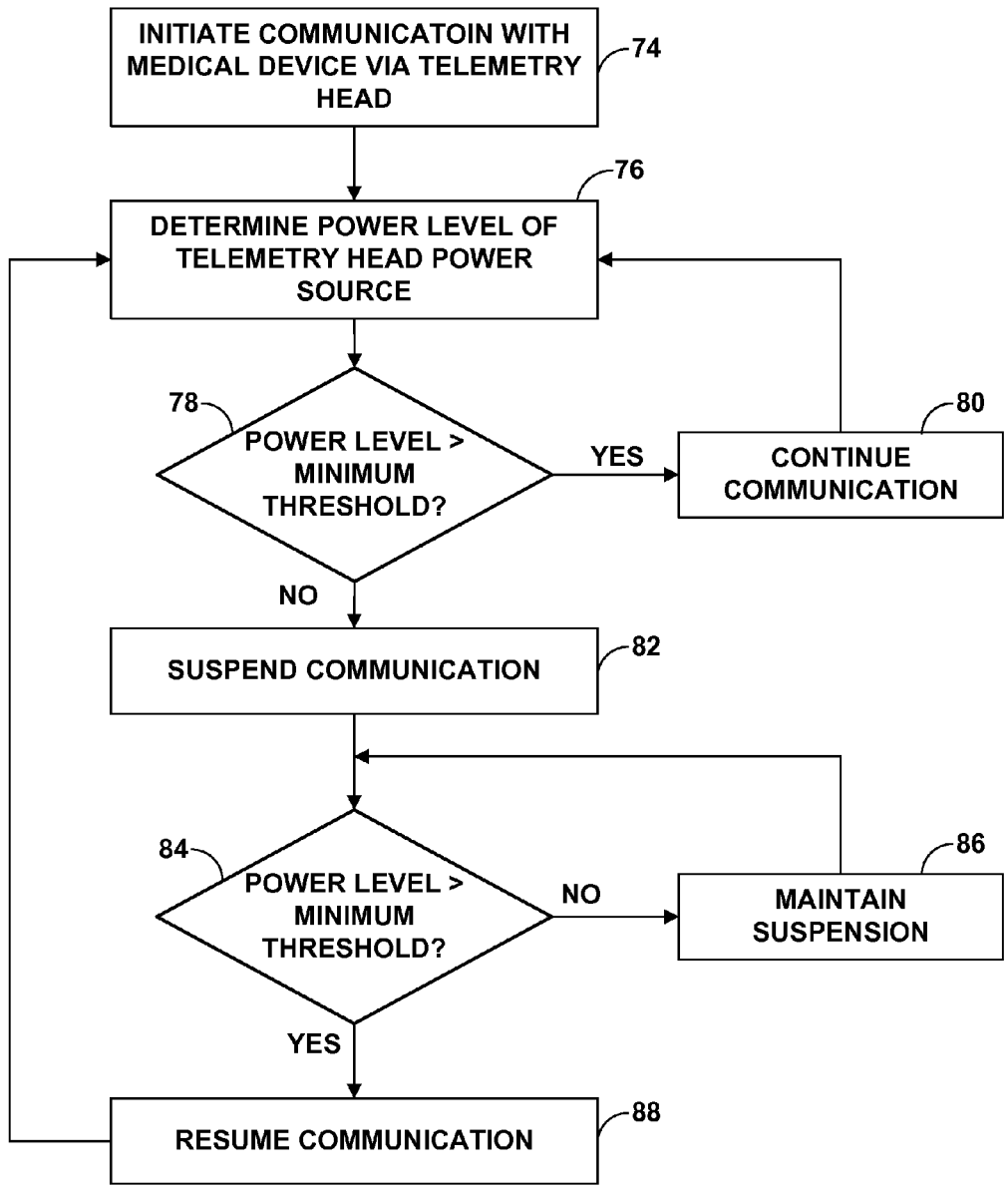
FIGS. 5-7 are flow diagrams illustrating example techniques in accordance with some aspects of the disclosure.

FIG. 5 is a flow diagram illustrating an example technique of the disclosure that may be employed in a system configured for wireless communication between an IMD and external programmer or another external device via an external telemetry head device. For ease of illustration, the example technique of FIG. 5, as well as the example techniques of FIGS. 6 and 7, will be described with regard to example medical device system 10 shown in FIG. 1. However, the techniques described herein may be employed with medical device systems including components other than that of medical device system 10.

As described above, in some examples, the power level of the telemetry head power source 72 may be monitored during a programming, interrogation or other wireless communication session in which data is communicated to and/or from programmer 20 and IMD 12 via telemetry head device 22. As shown in FIG. 5, processor 52 of programmer 20 may initiate communication with IMD 12, e.g., upon receipt of user instructions via user interface 50 to begin a programming session or other communication session with IMD 12 (74). To initiate communication, processor 52 may use telemetry module 56 to establish a wireless connection with programmer telemetry module 56 of external telemetry head device 22. In some examples, the connection between programmer 20 and telemetry head device 22 may first be established via a wired connection, e.g., to ensure that the connection is secure, and then the telemetry head device 22 may be unplugged from the programmer 20 while maintaining a wireless connection. In other cases, a secure connection between programmer 20 and telemetry head device 22 may be established via wireless communication, e.g., using one or more suitable wireless handshake protocols.

Once a wireless connection is established with telemetry head device 22, telemetry head device 22 may be positioned relative to IMD 12 in a manner that allows for IMD telemetry module 70 to establish a connection with telemetry module 30. Alternatively, the telemetry head device 22 may be positioned by a user in such a manner prior to the establishment of the connection between telemetry head device 22 and programmer 20. Regardless, processor 62 may use IMD telemetry module 70 to establish a wireless connection with telemetry module 30 of IMD 12, e.g., using a search and identification technique. In some examples, processor 62 may establish such a connection with IMD 12 upon receiving instructions to do so from programmer 20. Additionally or alternatively, processor 62 may establish such a connection with IMD 12 upon receiving instructions from a user via user interface 60 of telemetry head device 22.

Once processor 62 of telemetry head device 22 establishes a wireless connection with both programmer 20 and IMD 12, communication between programmer 20 and IMD 12 may be initiated by transferring data from programmer 20 to IMD 12, and vice versa, via telemetry head device 22 (74). In some examples, a substantially continuous connection between telemetry head device 22 and programmer 20, and telemetry head device 22 and IMD 12 may be maintained throughout the communication session. In some examples, a series of commands (both single and multiple) may be transmitted from programmer 20 to IMD 12 such that the session may be viewed as the periodic transmission smaller packets of data rather than the continuous flow of data from programmer 20 to IMD 12, and vice versa, via external telemetry device 22. The data transferred during interrogation may be include the transfer of instructions from programmer 20 to IMD 12 defining delivery of therapy from IMD 12 to patient 16 as well as the transfer of data from IMD 12 to programmer 20 regarding prior therapy delivered to patient 16 and/or data relating to one more physiological parameters sensed via IMD 12.

As described above, during a wireless interrogation session, programmer 20 may wirelessly interrogate IMD 12 using the wireless communication link established via external telemetry device 22. During an interrogation session, a series of commands (both single and multiple) may be sent to IMD 12 from the programmer 20 to read the current configuration of IMD 12, and additional data may be requested during the interrogation session. In such a scenario, the interrogation session may be viewed as the periodic transmission of smaller packets of data rather than the continuous flow of data from programmer 20 to IMD 12, and vice versa, via external telemetry device 22. The interrogation session may end when all the requested data is received by programmer 20 from IMD 12 and the wireless communication link is severed. In some examples, the interrogation session may be paused or suspended by stopping the transmission of the series of commands.

As also described above, during a programming session, programmer 20 may wirelessly program IMD 12 using the wireless communication link established via external telemetry head 22. During the programming session, a clinician may define one or more aspects or values of therapy parameters (e.g., by defining one or more therapy programs) using programmer 20 and write the data to IMD 12 using the wireless communication link established via external telemetry head device 22. In some examples, a clinician may modify some of the data received during interrogation of IMD 12 using programmer 20 and then write the data back to IMD 20 using the wireless communication link.

During the communication session, processor 62 may periodically or continuously determine the power level of power source 72 (76). For example, processor 62 may sample the voltage, current and/or some other signal of power source 72 periodically. To account for fluctuations in the sampled signal of power source 72, processor 62 may determine the power level of power source 72 by determining a rolling average of, e.g., the last ten sampled values. Alternatively, processor 62 may determine the power level value on a single sample basis. In another example, processor 62 may obtain a measurement from a measurement circuit such as a Coulomb counter that monitors the level of charge of power source 72. The power level determination may also be performed by processor 52 of programmer 20 based on data wirelessly transmitted from telemetry head device 22 to programmer 20 during communication.

Based on the determined power level, the wireless communication session may continue or be suspended. As shown in FIG. 5, for example, once the power level of power source 72 is determined (76), processor 52 or 62 may compare the determined power level to a minimum threshold value (78). Such a minimum threshold value may correspond to an amount of power that would not allow the telemetry head device to operate throughout the entire interrogation session. The minimum threshold value may be stored in memory 54 or memory 64, and may be predefined by a clinician and/or manufacturer of telemetry head device, e.g., based on evaluation of prior interrogation sessions. A minimum threshold power level may be globally applied or the threshold values unique to particular types of interrogation may be applied.

If processor 52 and/or processor 62 determine that the power level of power source 72 is greater than the minimum threshold level (78), wireless communication between programmer 20 and IMD 12 through telemetry head device 22 may continue (80). Since the power level of power supply 72 may decrease during a communication session, processor 52 and/or processor 62 may continue to monitor the power level and compare the power level to the minimum threshold level until the communication session is complete and data is no longer being transferred between programmer 20 and IMD 12.

Conversely, if processor 52 and/or processor 62 determine that the power level of power source 72 is less than the minimum threshold level (78), wireless communication between programmer 20 and IMD 12 through telemetry head device 22 may be suspended (82). While the communication is suspended (82), the power level of power supply 72 may be increased. For example, during the suspension, power source 72 of the wireless telemetry head device may be recharged by a user in the case in which the power source 72 includes one or more rechargeable batteries. As another example, power source 72 of the wireless telemetry head device may be replaced by a user with another power source 72, e.g., by switching out an existing battery of telemetry head device with a new battery having increased power level. As still another example, wireless telemetry head device 22 may be replaced with an entirely different wireless telemetry head device including another power source 72 with an increased power level. In such a case, processor 52 may transfer information to the processor of the new wireless telemetry device regarding the previously suspended communication (e.g., that may also been stored in the memory of the prior telemetry device 22) to allow for the wireless communication session to resume.

Once the power level has been increased to a level sufficient to allow the telemetry device to operate throughout the remainder of the communication session, the communication session may be resumed. Such a determination may be made by processor 52 and/or 62, e.g., upon a request by a user, by again determining the power level of power source 72 and comparing the minimum threshold level (84). If the new power level of power 72 is greater than the minimum threshold level, the suspended communication may be resumed (88). Alternatively, if the power level of power source 72 is still determined to be below the minimum threshold level, the communication may remain suspended (86). Such a determination may be made by processor 52, processor 62, and/or some other processor.

To the extent that wireless connection between programmer 20 and telemetry head device 22 and/or the wireless connection between IMD 12 and telemetry head device 22 was disconnected while the communication was suspended, those connections may be restored upon resuming the suspended interrogation (88). The communication between IMD 12 and programmer 20 via telemetry head device 22 may be resumed, e.g., at the point the communication was suspended, rather than requiring all of the data previously communicated prior to the suspension to be re-sent between IMD 12 and programmer 20 via telemetry head device 22 (88).

For example, the communication between programmer 20 and IMD 12 may include a command from programmer 20 and response to the command by IMD 12. If the power level of telemetry device battery supply 72 is determined to be too low, programmer 20 may suspend the transmission of commands until the power level of power source 72 has been increased to a level sufficient to allow telemetry device 22 to operate throughout the remainder of the communication session. Each command and response may share a sequence number so programmer 20 knows that, when resumed, it gets the proper response from IMD 12. With this information, programmer 20 can continue a communication session where it was suspended, because programmer 20 knows which command/response was last successfully completed. In some examples, programmer 20, IMD 12, and telemetry head device 22 may exchange security information (e.g., using a suitable wireless handshake technique) in order to resume the session.

In some examples, wireless communication between programmer 20 and IMD 12 may be suspended (82) by stopping the sending of data requests to IMD 12. When no data is being transmitted to the IMD 12, the programmer and telemetry head may send a "ping" to each other, validating the wireless communication path is still open. If telemetry head 22 is disconnected, e.g., when switching to another telemetry head device, programmer 20 may time out waiting for the PING response from IMD 12 and will indicate to the user that programmer 20 is no longer wirelessly connected with IMD 12.

In some examples, if the same telemetry head 22 is restored (e.g., by recharging power source 72 or replacing power source 72), telemetry head 22 may re-bond with programmer wirelessly and it will restart the communication with IMD 12, e.g., using information stored in the memory of telemetry head 22. If a new telemetry head is used, programmer 20 may first be connected via USB (or other wired connection) with the new telemetry head for the proper wireless configuration data to be passed back and forth. Once bonded via the wired connection, the wired connection can be removed and a wireless connection may be restored. In some examples, programmer 20 continues to try to "ping" telemetry head 22 and posts a message to the user via user interface 50. Once the wireless connection is restored, the suspended wireless communication session automatically continues where left off.

Throughout the technique of FIG. 5, programmer 20 may receive information from telemetry head 22 regarding power source 72. In some examples, a "ping" from programmer 20 to telemetry head 22 may include a request for information about the power level of telemetry head power source 72. The clinician may also be notified of the power level of telemetry head power source 72, as well, when programmer 20 loses its connection with telemetry head device 22 (e.g., via a disconnection of the wired interface or by turning off the telemetry head device 22)

By not ending the communication session but instead suspending the session, the power level of power source 72 may be increased without the need to exit the therapy programming session and reconfigure the system. In this manner, a clinician can be confident that a programming session or other communication session between programmer 20 and IMD 12 via telemetry head device 22 will not have to be ended prior to completion due to power source 72 not having enough power to complete the entire interrogation. Rather, the power level of power source 72 may be increased during the middle of a communication session as described herein. Once the communication session is resumed, stored information that describes the suspension will allow the transfer of data to continue at substantially the same point at which it was discontinued.

Figure 6:
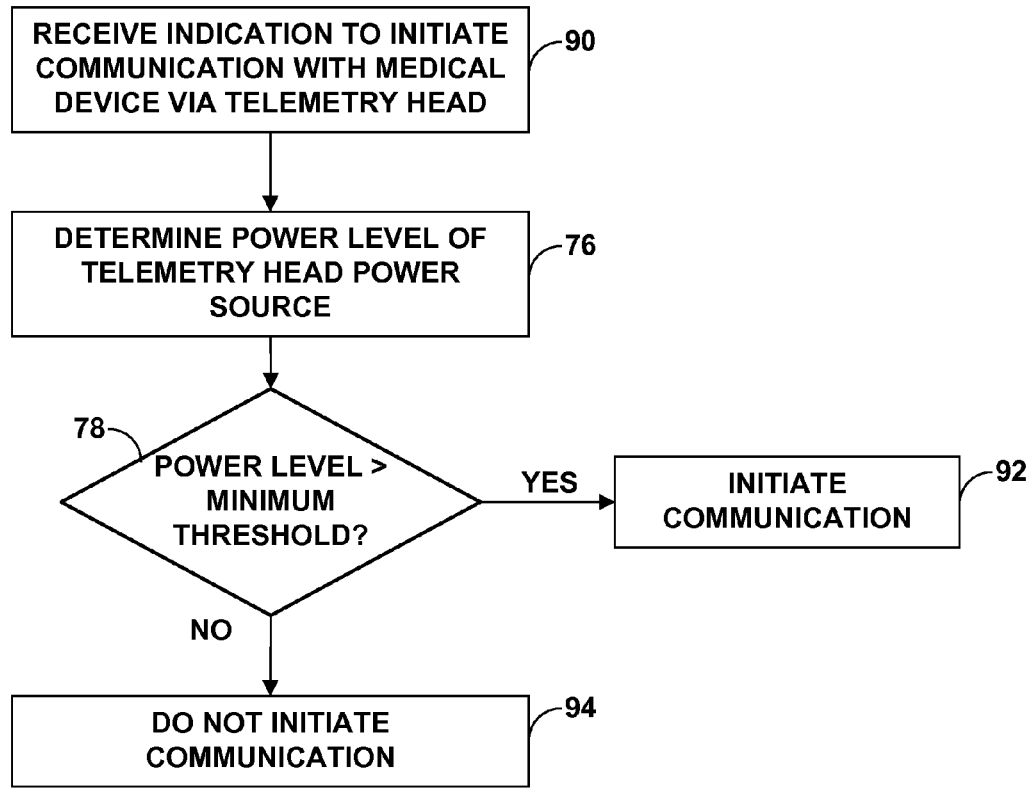

FIG. 6 is a flow diagram illustrating another example technique of the disclosure that may be employed in a system configured for wireless communication between IMD 12 and external programmer 20 via external telemetry head device 20. As shown in FIG. 6, processor 52 of programmer 20 may receive an indication from a clinician or other user indicating that communication between IMD 12 and programmer 20 via external telemetry head device 22 should be initiated (90). For example, such an indication may be received from the user via user interface 50 of programmer 20. In other examples, such as that described below with regard to FIG. 7, such an indication may be received from the user via user interface 60 of telemetry device 22.

Prior to initiating the requested wireless communication, processor 52 and/or processor 62 may determine power level of power source 72 of telemetry head device (76), and compare the determined power level to a minimum threshold level (78), e.g., in the manner described above with regard to the example of FIG. 5. The minimum threshold level may correspond to an amount of power that would not allow the telemetry head device to reliably operate throughout the entire communication session, or another amount within some predetermined margin of such amount of power that would not allow the telemetry head device to reliably operate throughout the entire communication session. The minimum threshold value may be stored in memory 54 or memory 64, and may be predefined by a clinician and/or manufacturer of telemetry head device, e.g., based on evaluation of prior communication sessions. A minimum threshold power level may be globally applied or the threshold values unique to particular types of communication (e.g., interrogation versus programming) may be applied.

If processor 52 and/or processor 62 determine that the power level of power source 72 is above the minimum threshold (78), the wireless communication may be initiated (92). For example, a wireless connection between programmer 20 and IMD 12 via telemetry head device 22 may be established and data may be transferred by the wireless connection in a one-way or two-way manner between programmer 20 and IMD 12. Conversely, if processor 52 and/or processor 62 determine that the power level of power source 72 is below the minimum threshold (78), the communication link may not be initiated (94). In such a situation, a message may be displayed to the user via user interface 50 of programmer 20 indicating to the user that the power level of power source 72 is not sufficient to operate telemetry head device 22 throughout an entire communication session. Upon receiving such a message, a user may increase the power level of power source 72 above the minimum threshold in order to begin wireless communication between IMD 12 and programmer 20, e.g., by recharging or replacing the power source, or using an entirely different telemetry head device with another power source. In this manner, a user may be prevented from beginning a programming or other communication session if the power level of power source 72 is not sufficient to operate telemetry head device 22 throughout an entire communication session. As such, the user will not be required to prematurely end a communication session or suspend the communication due to insufficient power to operate telemetry head device 22 in the manner described herein. Various examples of the disclosure may be within the scope of the following numbered aspects:

1. A method comprising receiving an indication to initiate wireless communication between a medical device and a medical device programmer or other external device (e.g., a cell phone, a tablet PC, and the like) via a telemetry head device, wherein the telemetry head device includes a power source configured to supply operational power to the telemetry head device; and determining, prior to initiating the communication between the medical device and the medical device programmer, a power level of the power source of the telemetry head device based on the receipt of the indication to initiate wireless communication, wherein at least one of the receiving and determining is performed via at least one processor.

2. The method of aspect 1, further comprising preventing initiation of the communication based on the determined power level.

3. The method of aspect 2, wherein preventing initiation of the wireless communication based on the determined power level comprises preventing initiation of the wireless communication based on a determination that the first power level is below a threshold power level.

4. The method of aspect 2, further comprising subsequently determining the power level of the power source has increased, and initiating wireless communication between the medical device and the programmer via telemetry head device based on the subsequent determination.

5. A system comprising a medical device programmer; a telemetry head device configured to wirelessly communicate with the medical device programmer, wherein the medical device programmer is configured to wirelessly communicate with a medical device via the telemetry head device, wherein the telemetry head device includes a power source configured to supply operational power to the telemetry head device; and a processor configured to receive an indication to initiate wireless communication between the medical device and the medical device programmer, and determine, prior to initiating the wireless communication of the medical device, a power level of the power source of the telemetry head device based on the receipt of the indication to initiate the wireless communication.

6. A system comprising means for receiving an indication to initiate wireless communication between a medical device and a medical device programmer via a telemetry head device, wherein the telemetry head device includes a power source configured to supply operational power to the telemetry head device; and means for determining, prior to initiating the communication between the medical device and the medical device programmer, a power level of the power source of the telemetry head device based on the receipt of the indication to initiate wireless communication.

7. A computer-readable storage medium comprising instructions that cause at least one processor to receive an indication to initiate wireless communication between a medical device and a medical device programmer via a telemetry head device, wherein the telemetry head device includes a power source configured to supply operational power to the telemetry head device; and determine, prior to initiating the communication between the medical device and the medical device programmer, a power level of the power source of the telemetry head device based on the receipt of the indication to initiate wireless communication, wherein at least one of the receiving and determining is performed via at least one processor.

Figure 7:
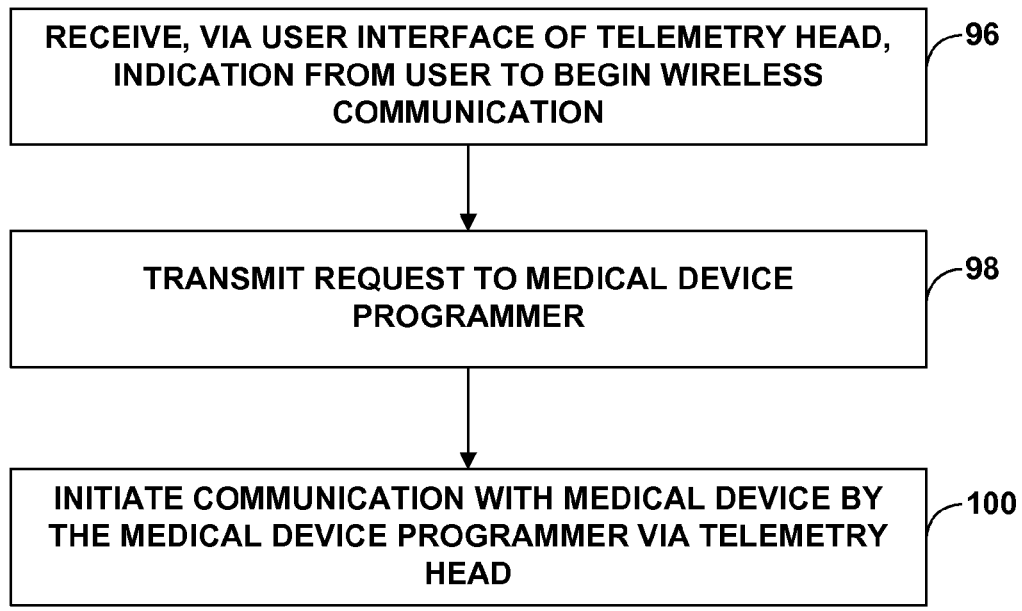

FIG. 7 is a flow diagram illustrating another example technique of the disclosure that may be employed in a system configured for wireless communication between an IMD and external programmer via an external telemetry head device. As shown in FIG. 7, rather than receiving input from a user via user interface 50 of programmer 20, user input may be received via user interface 60 of telemetry head device 22 indicating that wireless communication between IMD 12 and programmer 20 should be initiated (96). For example, user may depress a button dedicated to receiving such input or otherwise interact with user interface 62 of telemetry head device 22 to indicate to telemetry head device 22 that communication with IMD 12 should begin. A user may input such instructions upon determining that telemetry head device 22 is properly positioned relative to IMD 12 for wireless telemetry. For example, user interface 62 of telemetry head device 22 may present an indicator to a user indicating that a wireless communication link has been established with IMD 12.

Upon receipt of the indication (96), telemetry head device 22 may transmit instructions to programmer 20, e.g., via wireless communication, to initiate communication with IMD 12 (98). Programmer 20 may then initiate communication with IMD 12 via telemetry head device 22 (100). The communication between IMD 12 and programmer 20 via telemetry head device may be initiated, e.g., in the manner described with regard to the example process of FIG. 5. Using the process of FIG. 7, a user may initiate communication with IMD 12 without having to interact with programmer 20 after properly positioning wireless telemetry head device 22. Instead, a user may position telemetry head device 22 and initiate communication with IMD 12 by interacting only with telemetry head device 22. In some examples, wireless communication may only be initiated using interface 62 of telemetry head device 22 when programmer 20 is ready to start the wireless communication process.

In some examples, as a precaution, a user may be required to first provide authorization, e.g., via user interface 52 of programmer 20, that communication may be initiated through user interface 62 of telemetry device 22. In this manner, the use of user interface 62 of telemetry head to initiate communication with IMD 12 may be selectively enabled and disabled. In some example, authorization for initiation of communication via user interface 62 may automatically be revoked once a communication session of IMD 12 has ended. In other examples, a user must provide instructions, e.g., via user interface 52 and/or 62, to revoke any such prior authorization.

Various examples of the disclosure may be within the scope of the following numbered aspects:

1. A method comprising receiving an indication to initiate wireless communication between a medical device and an external device such as, e.g., a medical device programmer, wherein the indication is generated based on user input received via a user interface of a telemetry head device, wherein the medical device programmer is configured to wirelessly communicate with the medical device via the telemetry head device; and initiating wireless communication between the medical device and the medical device programmer via the telemetry head device based on receipt of the indication, wherein at least one of the receiving and initiating is performed via at least one processor. In some examples, the external device may be a device other than a dedicated programmer, such as a cellular phone, a tablet PC, or other device.

2. The method of aspect 1, further comprising receiving from a user interface of the medical device programmer authorizing the wireless communication between the medical device and medical device programmer be initiated via the indication received via the user interface of the telemetry head device.

3. The method of aspect 2, further comprising automatically removing the authorization upon ending of the wireless interrogation.

4. A system comprising a telemetry head device; a medical device programmer configured to wirelessly communicate with a medical device via the telemetry head device; and a processor configured to receive an indication to initiate wireless communication between the medical device and the medical device programmer, wherein the indication is generated based on user input received via a user interface of the telemetry head device, and initiate wireless communication between the medical device and the medical device programmer via the telemetry head device based on receipt of the indication.

5. A system comprising means for receiving an indication to initiate wireless communication between a medical device and a medical device programmer, wherein the indication is generated based on user input received via a user interface of a telemetry head device, wherein the medical device programmer is configured to wirelessly communicate with the medical device via the telemetry head device; and means for initiating wireless communication between the medical device and the medical device programmer via the telemetry head device based on receipt of the indication.

6. A computer-readable storage medium comprising instructions that cause at least one processor to receive an indication to initiate wireless communication between a medical device and a medical device programmer, wherein the indication is generated based on user input received via a user interface of a telemetry head device, wherein the medical device programmer is configured to wirelessly communicate with the medical device via the telemetry head device; and initiate wireless communication between the medical device and the medical device programmer via the telemetry head device based on receipt of the indication.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described herein. These and other examples are within the scope of the following claims.

The invention claimed is:

1. A method comprising:
wirelessly communicating, using an external medical device, with an implantable medical device via an external telemetry head device that is separate from the external medical device, wherein the external telemetry head device includes a power source configured to supply operational power to the external telemetry head device;
determining a first power level of the power source while the external medical device wirelessly communicates with the implantable medical device via the external telemetry head device;
suspending the wireless communication between the implantable medical device and the external medical device based on the determined first power level;
subsequently determining the power source increased to a second power level greater than the first power level; and
resuming the suspended wireless communication between the implantable medical device and the external medical device via the external telemetry head device based on the determined second power level of the power source, and
wherein at least one of the communicating, determining, and suspending is performed via at least one processor.

2. The method of claim 1, wherein the power source comprises a first power source, wherein subsequently determining the power source increased to a second power level greater than the first power level comprises determining the first power source has been replaced with a second power source defining the second power level.

3. The method of claim 2, wherein the external telemetry head device comprises a first external telemetry head device, wherein the second power source supplies power to a second external telemetry head device, and wherein resuming the suspended wireless communication between the implantable medical device and the external medical device via the external telemetry head device based on the determined second power level of the power source comprises resuming the suspended communication between the implantable medical device and the external medical device via the second external telemetry head device using the second power source.

4. The method of claim 2, wherein resuming the suspended wireless communication between the implantable medical device and the external medical device via the external telemetry head device based on the determined second power level of the power source comprises resuming the suspended wireless communication between the implantable medical device and the external medical device via the first external telemetry head device using the second power source.

5. The method of claim 1, further comprising determining that the power source has been recharged from the first power level to the second power level after suspending communication between the implantable medical device and the external medical device based on the determined first power level.

6. The method of claim 1, further comprising wirelessly transmitting an indication of the first power level from the external telemetry head device to the external medical device.

7. The method of claim 1, wherein suspending wireless communication between the implantable medical device and the external medical device based on the determined first power level comprises suspending wireless communication between the implantable medical device and the external medical device based on a determination that the first power level is below a threshold power level.

8. The method of claim 1, further comprising:
prior to suspending the wireless communication, presenting an indicator to a user via a user interface of the external medical device indicating the first power level of the power source to the user; and
receiving input from the user via the user interface indicating that the wireless communication should be suspended,
wherein suspending wireless communication between the implantable medical device and the external medical device based on the determined first power level comprises suspending wireless communication between the implantable medical device and the external medical device based on the input from the user.

9. The method of claim 1, wherein the external medical device comprises a medical device programmer.

10. The method of claim 1, wherein the external telemetry head device is configured to communicate with the external medical device via a wired telemetry connection.

11. The method of claim 1, wherein the external telemetry head device is configured to communicate with the external medical device via a wireless telemetry connection.

12. The method of claim 1, wherein the power source configured to supply operational power to the telemetry head device includes a first power source, and wherein the external medical device includes a second power source separate from the first power source, wherein the second power source is configured to supply operational power to the external medical device.

13. The method of claim 1, wherein determining the first power level of the power source while the external medical device wirelessly communicates with the implantable medical device via the external telemetry head device comprises determining a voltage value of the power source or a current value of the power source while the external medical device wirelessly communicates with the implantable medical device via the external telemetry head device.

14. The method of claim 13, further comprising:
comparing the determined first power level to a minimum threshold power level value; and
determining that the determined first power level is below the minimum threshold power level value based on the comparison, wherein suspending the wireless communication between the implantable medical device and the external medical device based on the determined first power level comprises suspending the wireless communication between the implantable medical device and the external medical device based on the determination that the determined first power level is below the minimum threshold power level value.

15. A system comprising:
an external medical device;
an external telemetry head device separate from the external medical device, wherein the external medical device is configured to wirelessly communicate with an implantable medical device via the external telemetry head device, wherein the external telemetry head device includes a power source configured to supply operational power to the external telemetry head device; and
at least one processor configured to determine a first power level of the power source while the external medical device wirelessly communicates with the implantable medical device via the external telemetry head device, suspend the wireless communication between the implantable medical device and the external medical device based on the determined first power level, subsequently determine the power source increased to a second power level greater than the first power level, and resume the suspended wireless communication between the implantable medical device and the external medical device via the external telemetry head device based on the determined second power level of the power source.

16. The system of claim 15, wherein the power source comprises a first power source, wherein the at least one processor is configured to determine the first power source has been replaced with a second power source defining the second power level.

17. The system of claim 16, wherein the external telemetry head device comprises a first external telemetry head device, wherein the second power source supplies power to a second external telemetry head device, and wherein the at least one processor is configured to resume the suspended communication between the implantable medical device and the external medical device via the external second telemetry head device using the second power source.

18. The system of claim 16, wherein the at least one processor is configured to resume the suspended wireless communication between the implantable medical device and the external medical device via the first external telemetry head device using the second power source.

19. The system of claim 15, wherein the at least one processor is configured to determine that the power source has been recharged from the first power level to the second power level after suspending communication between the implantable medical device and the external medical device based on the determined first power level.

20. The system of claim 15, wherein the telemetry head device is configured to transmit an indication of the first power level from the external telemetry head device to the external medical device.

21. The system of claim 15, wherein the at least one processor is configured to suspend the wireless communication between the implantable medical device and the external medical device based on a determination that the first power level is below a threshold power level.

22. The system of claim 15, wherein the at least one processor is configured to, prior to suspending the wireless communication, present an indicator to a user via a user interface of the external medical device indicating the first power level of the power source to the user, receive input from the user via the user interface indicating that the wireless communication should be suspended, and suspend the wireless communication between the medical device and the external medical device based on the input from the user.

23. The system of claim 15, wherein the external medical device comprises a medical device programmer.

24. The system of claim 15, wherein the at least one processor is contained within a housing of the external medical device.

25. The system of claim 15, wherein the external telemetry head device is configured to communicate with the external medical device via a wired telemetry connection.

26. The system of claim 15, wherein the external telemetry head device is configured to communicate with the external medical device via a wireless telemetry connection.

27. The system of claim 15, wherein the power source configured to supply operational power to the telemetry head device includes a first power source, and wherein the external medical device includes a second power source separate from the first power source, wherein the second power source is configured to supply operational power to the external medical device.

28. The system of claim 15, wherein the at least one processor is configured to determine at least one of a voltage value of the power source or a current value of the power source while the external medical device wirelessly communicates with the implantable medical device via the external telemetry head device, and suspend the wireless communication between the implantable medical device and the external medical device based on the at least one of the determined voltage or determined current value.

29. The system of claim 15, wherein the at least one processor is configured to:
compare the determined first power level to a minimum threshold power level;
determine that the determined first power level is below the minimum threshold power level value based on the comparison; and
suspend the wireless communication between the implantable medical device and the external medical device based on the determination that the determined first power level is below the minimum threshold power level value.

30. A system comprising:
means for wirelessly communicating, using an external medical device, with an implantable medical device via an external telemetry head device that is separate from the external medical device, wherein the external telemetry head device includes a power source configured to supply operational power to the external telemetry head device;
means for determining a first power level of the power source while the external medical device wirelessly communicates with the implantable medical device via the external telemetry head device;
means for suspending the wireless communication between the implantable medical device and the external medical device based on the determined first power level;
means for subsequently determining the power source increased to a second power level greater than the first power level; and
means for resuming the suspended wireless communication between the implantable medical device and the external medical device via the external telemetry head device based on the determined second power level of the power source.

* * * * *